United States Patent [19]

Farcasiu

[11] Patent Number: 4,672,147
[45] Date of Patent: Jun. 9, 1987

[54] METHOD FOR ISOMERIZING OLEFINS USING ACIDIC COMPOSITE CATALYSTS

[75] Inventor: Dan Farcasiu, Flemington, N.J.

[73] Assignee: Exxon Research and Engineering Company, Florham Park, N.J.

[21] Appl. No.: 848,257

[22] Filed: Apr. 4, 1986

Related U.S. Application Data

[63] Continuation-in-part of Ser. No. 705,988, Feb. 27, 1985, Pat. No. 4,585,750, which is a continuation-in-part of Ser. No. 563,818, Dec. 21, 1983, abandoned.

[51] Int. Cl.[4] .............................. C07C 5/25; C07C 5/27
[52] U.S. Cl. ...................................... 585/668; 585/671
[58] Field of Search ................ 585/668, 669, 664, 671

[56] References Cited

U.S. PATENT DOCUMENTS

| | | | |
|---|---|---|---|
| 3,770,567 | 11/1973 | Grot | 526/243 |
| 3,784,399 | 1/1974 | Grot | 526/243 |
| 3,849,243 | 11/1974 | Grot | 526/243 |
| 3,920,765 | 11/1975 | Frech et al. | 585/664 |
| 4,168,284 | 9/1979 | Conner | 585/668 |
| 4,482,775 | 11/1984 | Smith, Jr. | 585/671 |
| 4,585,750 | 4/1986 | Fareasiu | 502/159 |

Primary Examiner—Asok Pal
Attorney, Agent, or Firm—Jay Simon; E. Thomas Wheelock

[57] ABSTRACT

This invention provides a method for isomerizing olefins using a catalyst product which is a composite of a perfluorinated polymersulfonic acid and an anion-stabilizing agent such as hexafluoroisopropanol or trifluoroaetic acid. The composite catalyst has a significantly higher Bronsted acidity than the perfluorinated polymersulfonic acid.

10 Claims, No Drawings

METHOD FOR ISOMERIZING OLEFINS USING ACIDIC COMPOSITE CATALYSTS

CROSS-REFERENCE TO RELATED APPLICATIONS

This application is a continuation-in-part of U.S. Ser. No. 705,988, filed Feb. 27, 1985, now U.S. Pat. No. 4,585,750 which in turn is a continuation-in-part of U.S. Ser. No. 563,818, filed Dec. 21, 1983, now abandoned.

FIELD OF THE INVENTION

This invention provides a method for isomerizing olefins using a catalyst product which is a composite of a perfluorinated polymersulfonic acid and an ion-stabilizing agent such as hexafluoroisopropanol or trifluoroacetic acid. The composite catalyst has a significantly higher Bronsted acidity than the perfluorinated polymersulfonic acid.

BACKGROUND OF THE INVENTION

In the past hydrocarbon conversion reactions such as alkylations, acylations, rearrangements, and isomerizations were carried out in the presence of strong Lewis acids or strong Bronsted acids. A Lewis acid is a compound in which the normal electronic grouping about the central atom can accept an electron pair from a Lewis base which is any compound capable of donating an electron pair. Such Lewis acids include fluorides, chlorides, and bromides of aluminum, zinc, titanium, zirconium, antimony and iron. Bronsted acidity reflects the ability of a protonic acid to transfer a proton to a base. Bronsted acids suitable as catalysts for hydrocarbon conversion reactions include strong acids such as liquid sulfuric acid, hydrogen fluoride, phosphoric acid and trifluoromethanesulfonic acid. Generally these protonic acids have an $H_o$ value on the Hammett scale of $-11$ or less. The effectiveness of such Lewis acid and Bronsted acid catalysts for hydrocarbon conversions is directly related to the acidity of the catalyst material toward the hydrocarbon substrate.

Although these Lewis acids and Bronsted acids perform satisfactorily as catalysts for hydrocarbon conversion reactions they suffer from certain disadvantages. Lewis acids form colored hydrocarbon complexes with the anionic components formed during the hydrocarbon conversion reaction and molar amounts are normally required. Work-up is also needed to decompose these complexes and the catalyst is usually non-recoverable. Strong protonic Bronsted acids, on the other hand, form insoluble sludges as products during the reaction which are extremely difficult to separate.

In order to overcome these disadvantages solid acids such as perfluorinated polymersulfonic acids have been employed as catalysts for hydrocarbon conversion reactions. Such acids have acidities of greater than $-11\ H_o$ on the Hammett scale. These solid super acids do not form complexes or insoluble sludges and can be easily separated from the reaction mixture by filtration and regenerated without loss of activity. In addition these super acids can be used in catalytic amounts, are highly stable and maintain long range catalytic activity.

Solid superacidic perfluorinated polymersulfonic acids, sold under the trademarks NAFION or PFIEP by E.I. Dupont De Nemours have been applied in organic synthesis for a variety of reactions including the alkylation of arenes with alkenes, alkyl halides, alcohols and esters; transalkylation of arenes with polyalkyl benzenes; acylation, sulfonation, and halogenation reactions; preparation of acetals, the synthesis of cyclic ethers; the preparation of $\alpha,\beta$-unsaturated carbonyl compounds and methoxy methyl ethers; the preparation of 1,1-diacetates from aldehydes; the pinacolone rearrangement; the hydration of lower olefins, the nitration of aromatic compounds; and the isomerization, disproportionation and transmethylation of methylbenzene. Common to all these acid catalyzed reactions is the formation of carbocations as intermediates.

Perfluorinated polymersulfonic acids of the NAFION or PFIEP type contain a repeating structure represented by either of the following formulae:

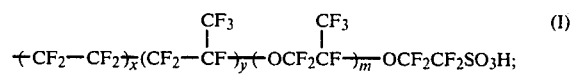

or

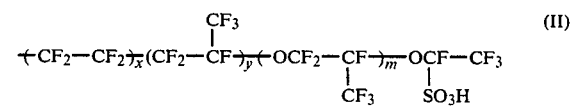

wherein the ratio of x over y varies from 2 to 50 and m is 1 or 2. The above formulae (I) and (II) are in accordance with the specification of Great Britain Pat. No. 2,082,178. The molecular weight of these polymers range from about 1000 to 500,000 daltons and the sulfonic acid groups comprise from about 0.01 to 5 mequiv/gram of catalyst.

The catalysts are prepared by polymerizing the corresponding perfluorinated vinyl compounds according to the methods disclosed in U.S. Pat. Nos. 3,282,875 and 3,882,093. U.S. Pat. No. 4,041,090 discusses the structure and describes a method for preparing the perfluorinated polymersulfonic acid by copolymerizing the corresponding perfluorinated vinyl ethers with perfluoroethylene and/or perfluoro alpha olefins.

The acidity of such superacidic perfluorinated polymersulfonic acids can be significantly enhanced by treating the solid surface of the resin with certain anion-stabilizing agents to form the catalyst product or phase used in this olefin isomerization process. These agents were denominated "ion-stabilizing" agents in the parent applications.

SUMMARY OF THE INVENTION

The catalyst product used in the olefin isomerization process of this invention is a composite of a perfluorinated polymersulfonic acid and anion-stabilizing agent such as trifluoroacetic acid or hexafluoroisopropanol in which the polymersulfonic acid is essentially impregnated with the anion-stabilizing agent. Such catalyst composite is prepared by contacting the perfluorinated polymersulfonic acid with a liquid anion-stabilizing agent or a solution of the anion-stabilizing agent in a polar inert solvent such as chloroform or methylene chloride. The acidity of the so-formed catalyst composite is significantly higher than either the perfluorinated polymersulfonic acid component alone or the anion-stabilizing agent component alone such that the composite will protonate a standard base, hexamethylbenzene, but the individual components of the composite will not.

The catalyst composite is useful as a catalyst for olefin isomerization reactions. It has been found that by employing the catalyst composite in such a reaction, the rate of double bond migration along a carbon chain, e.g., isomerization, is about 100 times faster than the same reaction catalyzed with the perfluorinated polymersulfonic acid alone.

DETAILED DESCRIPTION OF THE INVENTION

The superacidic catalyst used in this invention comprises a composite of a solid acid, particularly a perfluorinated polymersulfonic acid, and at least one anion-stabilizing agent such as trifluoroacetic acid (TFA) or hexafluoroisopropanol (HFIP) which can be combined as a liquid or dissolved in an inert solvent such as a liquid halogenated hydrocarbon, as for example chloroform or dichloromethane (methylene chloride). An anion-stabilizing agent as used herein is a highly polar substance which can interact with ions by a mechanism such as solvation to make the ions more stable.

The anion-stabilizing agent utilized can be defined by its ability to interact with the perfluorinated polymersulfonic acid to generate a composite of significantly higher acidity than either the anion-stabilizing agent or the polymersulfonic acid by itself. Such anion-stabilizing agents may also be referred to as "acidity enhancers" but anion-stabilizing agent is preferred because the latter term is indicative of what is believed to be the mechanism of interaction between the agent and the polymersulfonic acid. While not wishing to be bound by any particular theory, we believe that the agent interacts with the anion resulting from the transfer of a proton from the original polymersulfonic acid (AH) to a base (B):

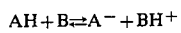

$$AH + B \rightleftharpoons A^- + BH^+$$

$$AH + B + S \rightleftharpoons [A^- \ldots S] + BH^+$$

As a consequence, the degree of protonation of the base, which represents the acidity of the polymersulfonic acid, increases in the presence of the agent(s).

The interaction between the anion $A^-$ and the agents is believed to be dipolar in nature, probably by hydrogen bonds, but no chemical (covalent) bond is formed between $A^-$ and S. The agents also must not be basic towards AH, that is, S must not interact with the proton transferred to the base B. For the higher acidic range achieved by use of the anion-stabilizing agent the properties of the agent, as demonstrated herein, are shown by fluorinated carboxylic acids, such as but not limited to the trifluoroacetic acid and by fluorinated alcohols, such as but not limited to hexafluoroisopropanol. Thus, anion-stabilizing agents that can be used in this invention are polar compounds (in the sense of forming a hydrogen bond with an anion) comprising fluorinated carboxylic acids and fluorinated alcohols, preferably $C_2$ to $C_6$ acids and alcohols, more preferably acids and alcohols that are polyfluorinated, or are of 2 to 4 carbon atoms.

Superacidic strength cannot be manifested in reactions in which water is a reactant or a product, since the strongest acid existing under such conditions is the hydronium ion, ($H_3O^+$), which is weaker than sulfuric acid. By contrast, reactions involving only hydrocarbons are generally considered to require catalysts of superacidic strength. It is well known in the art that such reactions involve carbocations as intermediates. The strength of a super acid can be evaluated from the extent to which a standard base is protonated by the super acid for a given initial acid/base ratio. Aromatic hydrocarbons are convenient standard bases for evaluation of superacidic strength. The amount of protonated aromatic present at equilibrium can be determined by carbon-13 nuclear magnetic resonance, hereafter $^{13}$C-NMR.

The acidity of the catalyst composite of this invention is evaluated by the degree of protonation of hexamethylbenzene (HMB) as the standard base, according to equation (III) below.

$$C_6Me_6 + [H^+] \rightleftharpoons C_6Me_6H^+ \qquad (III)$$

For the purpose of equation (III), $[H^+]$ represents any acid (source of proton) that can transfer its proton to a base, in this case HMB.

When a perfluorinated polymersulfonic acid is contacted with HMB, two signals appear in the $^{13}$C-NMR spectra at different chemical shifts; one signal attributable to the aliphatic carbon in the acid and the other attributable to the carbon atom attached to the benzene ring of HMB. Similarly, when an anion-stabilizing agent such as trifluoroacetic acid is contacted with HMB two signals at different chemical shifts are produced for the same reasons. However, when a catalyst composite is formed according to the invention from a perfluorinated polymersulfonic acid and an anion-stabilizing agent, a multiplicity of signals are exhibited which can be time-averaged to define two pairs of signals at different chemical shifts indicating that there are two kinds of hexamethylbenzene present, a protonated and an unprotonated hexamethyl-benzene.

The degree of protonation of a catalyst composite according to the invention can be determined by interpolation of the $^{13}$C-NMR spectra of HMB on the catalyst, between the spectrum of HMB in a non-acidic solution, and the spectrum of HMB in a super acid such as fluorosulfonic acid and antimony pentafluoride ($FSO_3H$-$SbF_5$) or a large excess of trifluoromethane sulfonic acid ($CF_3SO_3H$), in which HMB is fully protonated.

The catalyst composite can be prepared in a number of ways. The perfluorinated polymersulfonic acid can be combined with a solution of the anion-stabilizing agent in a polar, inert solvent, such as chloroform or dichloromethane and the polar solvent evaporated, or the anion-stabilizing agent in liquid form can be combined with the polymersulfonic acid. The catalyst composite may also be made by mixing the perfluorinated polymersulfonic acid with a mixture of the anion-stabilizing agent and its anhydride.

Generally the amount of anion-stabilizing agent should constitute from 10% to 500% by weight of the perfluorinated polymersulfonic acid or stated otherwise, the weight ratio of anion-stabilizing agent to perfluorinated polymersulfonic acid is from about 0.1 to 1 to 5 to 1.

The composite of perfluorinated polymersulfonic acid and ion-stabilizing agent, according to the invention, is useful as a catalyst for carbocationic (acid-catalyzed) processes such as the isomerization by double bond shift in an alkene. The composite catalyst has a better activity, that is, promotes a higher reaction rate, than the perfluorinated polymersulfonic acid alone. The composite catalyst is useful in all those carbocationic organic reactions for which the superacidic perfluorinated polymersulfonic acid has been previously used.

To employ the catalyst in a hydrocarbon conversion reaction, solid perfluorinated polymersulfonic acid is first combined with the anion-stabilizing agent to generate the composite catalyst, then the hydrocarbon conversion reactants are contacted with the so-formed composite catalyst under reaction conditions to effect the reaction.

The conversion process is operable on substituted or unsubstituted olefinic compounds. Preferred are $C_4$ to $C_{54}$ olefins. They may be linear, branched or contain aryl substituents. The olefinic materials may contain heteroatoms such as S, N or O. The temperature of conversion may be between 0° to 100° C. The range of 10° to 50° C. is preferred although ambient temperature is most proferred. The amount of catalyst controls the production rate. Suitable amounts are 20–500 moles olefin/equivalent solid acid group on the catalyst. A preferred range is 30–100 moles olefin/equivalent solid acid group.

When using a catalyst composite according to the invention as a catalyst for hydrocarbon conversion reactions such as the isomerization of olefins the rate is much faster than using the perfluorinated polymersulfonic acid alone.

EXAMPLE 1

This Example demonstrates the lack of protonating ability of HMB of each of two anion-stabilizing agents, trifluoroacetic acid (TFA), and hexafluoroisopropanol (HFIP) compared to a standard strong acid, trifluoromethanesulfonic acid and demonstrates the application of $^{13}$C-NMR to calculate the degree of protonation of HMB.

In this and in the following examples, the HFIP was dried on molecular sieves 3A, the chloroform was distilled from phosphorus pentoxide, and the TFA was mixed with 10% of its anhydride, boiled under reflux for 15 minutes, then fractionally distilled. To the distilled acid, 0.5–1% anhydride was added. All materials were stored under nitrogen in a dry-box, and all the samples were prepared inside the same dry-box. Contamination by air and moisture was carefully avoided during NMR analyses.

(a) Hexamethylbenzene (0.09 g) was dissolved in a mixture of HFIP (1.2 mL) and chloroform (0.2 mL). The $^{13}$C-NMR spectrum of the solution had signals at 132.84 ppm (aromatic carbon) and 14.90 ppm (methyl carbon) ppm from external/coaxial tetramethylsilane. No evidence of protonation of HMB was shown.

(b) Hexamethylbenzene (0.08 g) was dissolved in 1 mL of a 75:25 (v:v) mixture of TFA and chloroform. $^{13}$C-NMR signals for HMB were recorded at 131.81 ppm and 15.20 ppm indicating no protonation of HMB.

(c) Hexamethylbenzene (0.162 g) was dissolved in 2 mL of trifluoromethanesulfonic acid. The $^{13}$C-NMR spectrum of protonated HMB exhibited 7 signals at −60° C. 192.3 (2 carbons), 190.5 (1 carbon) 138.5 (2 carbons), and 56.0 (1 carbon) for the ring carbon atoms, and 23.3 (3 carbons), 19.7 (2 carbons), and 13.6 ppm (1 carbon), for the methyl carbon atoms. These became time-averaged at +50°, to exhibit 2 signals, at 151.9 and 19.09 ppm, for the ring, and methyl carbons, respectively.

Comparison between the peak positions (chemical shifts), in case (c) and in case (a) or (b), shows the effect of protonation of HMB by trifluoromethanesulfonic acid.

(d) Hexamethylbenzene (0.163 g, 1.006 mmol) was mixed with 1 mL of an 88:12 (v/v) HFIP-chloroform mixture; trifluoromethanesulfonic acid (0.185 g, 1.233 mmol), then more HFIP-chloroform mixture (1.5 mL) was added. $_{13}$C-NMR signals at 50° C. were located at 136.30 and 15.71 ppm. Interpolation using the values in Example 1(a) and 1(c) indicated approximately 19% protonation of HMB by the trifluoromethanesulfonic acid.

EXAMPLE 2a, b & c

This Example demonstrates that a perfluorinated polymersulfonic acid alone will not protonate hexamethylbenzene.

In this and in the following Examples the potassium salt of the perfluorinated polymersulfonic acid (E.I. DuPont PFIEP resin 511X) was converted to the acid form with hydrochloric acid, washed with water, and dried under nitrogen in a vacuum oven for 11 hours at 110°–115°. Titration with sodium hydroxide solution gave for various batches an acidity content of 0.86–0.91 mequiv/g. On thermogravimetric analysis, the material lost 0.1% weight at 100°, 1.0% at 200°, and 2% at 300°.

EXAMPLE 2(a)

One gram of dry solid perfluorinated polymersulfonic acid was treated with a solution of 0.10 g of HMB in dry methylene chloride for up to 25 hours. Evaporation of solvent under vacuum gave a solid mixture which was transferred to the sample holder of a solid-state $^{13}$C-NMR instrument. The chemical shifts measured for HMB in this mixture (132.47, 17.39 ppm) did not differ from a sample in which HMB was mixed with an inert solid, silica gel (132.67, 17.59 ppm). No difference was observed when the HMB-solid acid mixture was ground prior to the NMR analysis. This indicates no protonation occurred in the solid acid.

EXAMPLE 2(b)

This experiment was similar to that of Example 2(a) except that the solid acid (1.51 g) was ground before the addition of HMB (0.05 g) dissolved in chloroform. The solvent was evaporated 89 hours after mixing. The HMB in the solid residue had $^{13}$C-NMR signals at 131.88 and 17.06 ppm, indicating that no protonation took place.

EXAMPLE 2(c)

This experiment was similar to that of Example 2(b), except that chloroform (0.6 mL) was not evaporated from the sample containing 0.052 g HMB and 1.000 g of solid acid. The $^{13}$C-NMR spectrum was run 96 hours after mixing, on a solution NMR instrument. The HMB signals appeared at 132.62 and 17.34 ppm. The relevant portions of the spectrum contained the signal of chloroform and of the external reference (tetramethylsilane) and lock solvent (deuterochloroform). Comparison with the spectrum of HMB on silica gel or in chloroform solution indicated again that no protonation occurred.

EXAMPLE 3

This Example illustrates the preparation of a catalyst composite according to the invention in situ from a perfluorinated polymersulfonic acid and trifluoroacetic acid in chloroform and demonstrates the composite's ability to protonate hexamethylbenzene.

Exactly 1.01 g of dry and ground solid perfluorinated polymersulfonic acid was combined with a solution of 0.039 g of hexamethylbenzene in 0.7 mL of a solution of 75% by volume of trifluoroacetic acid and 25% by volume of dry chloroform. The $^{13}$C-NMR at 50° C. indicated that two kinds of HMB were present in the mixture. One pair of signals (132.66, 15.60 ppm) were attributed to unprotonated HMB in solution. The other pair of signals (135.80, 15.95 ppm) were attributed to the time averaged spectrum of partially protonated HMB, the degree of protonation of which was estimated at 13±3%. Such a spectrum requires that there are two kinds of molecules of HMB in the sample (A and B), and that the exchange of an HMB molecule from kind A to kind B is slow on NMR time scale. On the other hand, the protonation-deprotonation equilibrium must be fast on the NMR time scale, in order to lead to a time-averaged signal for the HMB molecules of kind B. These observations demonstrate that addition of the anion-stabilizing agent, trifluoroacetic acid, in the experiment has generated a new phase or composite comprising interacted anion-stabilizing agent and solid acid in which hexamethylbenzene is partially protonated (super acid phase B). The rest of HMB is found in a bulk solution phase (A), not different from the solution formed in the absence of the anion-stabilizing agent.

EXAMPLE 4

This Example demonstrates that, in the composite catalyst, according to the invention, the strongly acidic or superacidic phase (b) which is generated, is associated with the solid perfluorinated polymersulfonic acid and contains the anion-stabilizing agent, trifluoroacetic acid.

This experiment was similar to Example 3 except that a larger sample was prepared (0.071 g HMB, 1.52 g PFIEP resin, i.e. solid acid, and 1.2 mL of the 75:25 TFA-chloroform mixture). At the end of the experiment, the mixture was dumped onto a fine glass frit, which adsorbed the liquid and thereby separated out the bulk solution phase (A). The solid, still wet, was transferred quickly to another NMR tube and a new spectrum was recorded. The spectrum showed signals of the anion-stabilizing agent but not of the inert solvent, chloroform. Moreover, the average signal for the partially protonated HMB at 134.79 ppm exhibited an increase in relative intensity, while the signal for the aromatic carbon of unprotonated HMB was not observed.

EXAMPLE 5

This experiment was similar to that of Example 4, except that the solvent employed was the HFIP-chloroform mixture of Example 1(a). The quantities of reagents were 0.042 g HMB and 0.915 g solid acid (PFIEP) in 2 ml of solvent. The $^{13}$C-NMR spectrum was run 4 days after the preparation of the sample. The signals for HMB in phase A appeared at 133.87 ppm and 15.01 ppm; the signals for HMB in phase B appeared time averaged at 140.69 ppm and 16.47 ppm. The degree of protonation of HMB in phase B was evaluated at 38%.

The following Example illustrates the increase in the rate of olefin isomerization using the catalyst composite of the invention.

EXAMPLE 6

Dry Nafion (DuPont) (0.105 g) was covered with trifluoroacetic acid in a vial containing a magnetic stirring bar, and left for 90 hours, capped, in a dry box. The excess of trifluoroacetic acid was removed by blowing nitrogen, the vial was capped with a rubber septum, and 1-hexene (0.4 mL) was added with a syringe. The mixture was stirred at room temperature. Samples were withdrawn at intervals, through the septum, and analyzed by GLC on a 30 m 0.25 mm I.D. fused silica capillary column, coated with 0.25 μm film of methylphenyl (95:5) silicone, DB5 at 36° C. The results are shown in Table 1, entry 1.

EXAMPLE 7

The experiment of Example 6 was repeated, except that the trifluoroacetic acid treatment of the catalyst was omitted. The results are shown in Table 1, entry 2.

One can see that less conversion is achieved in 2 hours with the non-activated catalyst than in 40 sec. with the catalyst activated with TFA.

TABLE 1

| UNCONVERTED 1-HEXENE (%) IN THE MIXTURE WITH 2-/3-HEXENE | | | | | | |
|---|---|---|---|---|---|---|
| Time, h Run No. | 0.0 | 0.1 | 0.43 | 0.80 | 1.90 | 4.35 |
| 1. (TFA) | 100.0 | 94.4 | 22.0 | 12.0 | 2.3 | — |
| 2. (Un-treated) | 100.0 | | | | 99.0 | 87.9 |

I claim as my invention:

1. A method for isomerizing olefins comprising the steps of contacting at least one olefin with a catalyst composite comprising a perfluorinated-polymersulfonic acid and an anion-stabilizing agent and recovering the isomerized olefins.

2. The method of claim 1 wherein the catalyst composite contains an anion-stabilizing agent selected from the group consisting of $C_2-C_6$ fluorinated carboxylic acids and alcohols.

3. The method of claim 2 wherein the anion-stabilizing agent has 2 to 4 carbon atoms.

4. The method of claim 3 wherein the anion-stabilizing agent is polyfluorinated.

5. The method of claim 1 wherein the anion-stabilizing agent is trifluoroacetic acid.

6. The method of claim 1 wherein the anion-stabilizing agent is hexafluoroisopropanol.

7. The method of claim 1 wherein said perfluorinated polymersulfonic acid is represented by either of the formulae:

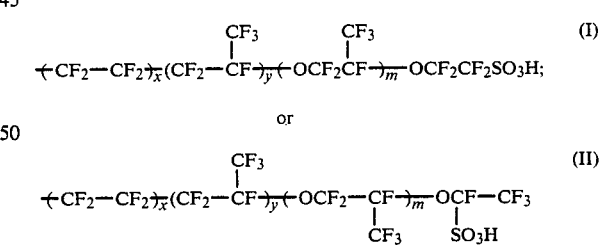

wherein the ratio of x over y varies from 2 to 50 and m is 1 or 2.

8. The method of claim 1 wherein the weight ratio of anion-stabilizing agent to perfluorinated polymersulfonic acid is from 0.1 to 1 to 5.0 to 1.

9. A method for isomerizing olefins comprising the steps of contacting at least one olefin with a catalyst composite comprising a perfluorinated polymersulfonic acid and an anion-stabilizing agent consisting of hexafluoroisopropanol or trifluoroacetic acid and recovering the isomerized olefins.

10. A method for isomerizing olefins comprising the steps of contacting at least one olefin with a catalyst composite comprising a perfluorinated polymersulfonic acid represented by either of the formulae:

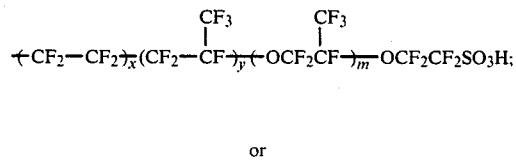

or

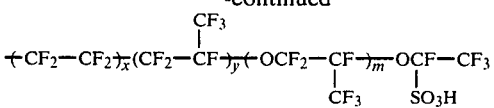

wherein the ratio of x over y varies from 2 to 50 and m is 1 or 2 and an anion-stabilizing agent selected from the group consisting of trifluoroisopropanol and trifluoroacetic acid; wherein the weight ratio of perfluorinated polymersulfonic acid to anion-stabilizing agent is from about 0.1 to 1 to 5.0 to 1, and recovering the isomerized olefin.

* * * * *